(12) United States Patent
Takada et al.

(10) Patent No.: US 11,499,136 B2
(45) Date of Patent: Nov. 15, 2022

(54) CELL CULTURE SUBSTRATE

(71) Applicant: FUJIFILM Corporation, Tokyo (JP)

(72) Inventors: Tetsuo Takada, Sakura (JP); Naoto Sakurai, Sakura (JP); Ayako Isshiki, Sakura (JP); Noriko Santou, Sakura (JP)

(73) Assignee: DIC Corporation, Tokyo (JP)

( * ) Notice: Subject to any disclaimer, the term of this patent is extended or adjusted under 35 U.S.C. 154(b) by 137 days.

(21) Appl. No.: 16/467,535

(22) PCT Filed: Dec. 12, 2017

(86) PCT No.: PCT/JP2017/044509
§ 371 (c)(1),
(2) Date: Jun. 7, 2019

(87) PCT Pub. No.: WO2018/116905
PCT Pub. Date: Jun. 28, 2018

(65) Prior Publication Data
US 2020/0063094 A1 Feb. 27, 2020

(30) Foreign Application Priority Data

Dec. 22, 2016 (JP) .............................. JP2016-248894

(51) Int. Cl.
| C12N 5/00 | (2006.01) |
| C01B 33/44 | (2006.01) |
| C08L 33/14 | (2006.01) |
| C08L 33/24 | (2006.01) |
| C08L 39/06 | (2006.01) |
| C09D 133/26 | (2006.01) |
| C12M 1/12 | (2006.01) |

(52) U.S. Cl.
CPC ............ *C12N 5/0068* (2013.01); *C01B 33/44* (2013.01); *C08L 33/14* (2013.01); *C08L 33/24* (2013.01); *C08L 39/06* (2013.01); *C09D 133/26* (2013.01); *C12M 25/14* (2013.01); *C12N 2533/32* (2013.01); *C12N 2533/70* (2013.01)

(58) Field of Classification Search
CPC .......... C01B 33/44; C08L 33/14; C08L 39/06; C08L 33/24; C12M 3/00; C12M 25/14; C12N 5/0068; C12N 2533/32; C12N 2533/70; C09D 133/26
See application file for complete search history.

(56) References Cited

U.S. PATENT DOCUMENTS

| 8,530,564 B2 * | 9/2013 | Takada ............... C08F 2/44 524/446 |
| 2006/0148958 A1 | 7/2006 | Haraguchi et al. |
| 2009/0120326 A1 | 5/2009 | Inoue et al. |
| 2010/0273667 A1 | 10/2010 | Kotov et al. |
| 2011/0033928 A1 | 2/2011 | Smith et al. |
| 2012/0015440 A1 | 1/2012 | Otsuka et al. |
| 2013/0101659 A1 | 4/2013 | Sawa et al. |
| 2016/0137965 A1 | 5/2016 | Sekiguchi et al. |
| 2017/0029763 A1 | 2/2017 | Takada |

FOREIGN PATENT DOCUMENTS

| CN | 102056983 A | 5/2011 |
| CN | 102597217 A | 7/2012 |
| CN | 103209717 A | 7/2013 |
| CN | 106164257 A | 11/2016 |
| EP | 1993731 A1 | 11/2008 |
| EP | 2292691 A1 | 3/2011 |
| JP | 2007-049918 A | 3/2007 |
| JP | 2010-017128 A | 1/2010 |
| JP | 2011-144236 A | 7/2011 |
| JP | 2013-194084 A | 9/2013 |
| JP | 2014-108093 A | 6/2014 |
| JP | 2015-519902 A | 7/2015 |
| JP | 2015-165921 A | 9/2015 |
| JP | 2016-039806 A | 3/2016 |
| JP | 2016-193976 A | 11/2016 |
| JP | 2016-194054 A | 11/2016 |
| WO | 2010027081 A1 | 3/2010 |
| WO | 2011043405 A1 | 4/2011 |
| WO | 2014199754 A1 | 12/2014 |
| WO | 2015093393 A1 | 6/2015 |

OTHER PUBLICATIONS

K. Haraguchi. Development of Soft Nanocomposite Materials and Their Applications in Cell Culture and Tissue Engineering. J Stem Cells Regen Med (2012), 8(1), 2-11. (Year: 2012).*
Liu et al. Lower critical solution temperatures of N-substituted acrylamide copolymers in aqueous solutions. Polymer (1999), 40, 6985-6990. (Year: 1999).*
T. Takehisa et al., "Cell Cultivation and Detachment on Nanocomposite Hydrogels with collagen and RGD," Polymer Preprints, Japan, vol. 55, No. 2, 2006, pp. 5069-5070 and English abstract. (cited in the ISR).
H. Fujita et al., "Application of a Cell Sheet-Polymer Film Complex With Temperature Sensitivity for Increased Mechanical Strength and Cell Alignment Capability," Biotechnology Bioengineering., 2009, vol. 103, No. 2, pp. 370-377 (cited in the ISR).
International Search Report dated Mar. 20, 2018, issued for PCT/JP2017/044509.

(Continued)

*Primary Examiner* — Sean C. Barron
(74) *Attorney, Agent, or Firm* — Locke Lord LLP; James E. Armstrong, IV; Nicholas J. DiCeglie, Jr.

(57) ABSTRACT

The present invention provides a cell culture substrate including a polymer having a lower critical solution temperature, the substrate including one or more inorganic materials selected from a water-swellable clay mineral and silica and further including an adhesive matrix in the substrate, in which the adhesive matrix is an extracellular matrix and/or an adhesive synthetic matrix. Furthermore, the invention is to provide a cell culture substrate in which the extracellular matrix is at least one selected from laminin, fibronectin, vitronectin, cadherin, and fragments thereof, and/or the adhesive synthetic matrix is poly[2-(methacryloyloxy)ethyl dimethyl-(3-sulfopropyl) ammonium hydroxide] or an oligopeptide-supporting polymer.

13 Claims, No Drawings

(56) References Cited

OTHER PUBLICATIONS

Rzhepishevska et al. "The Surface charge of anti-bacterial coatings alters motility and biofilm architecture" Biomater. Sci., 2013, 1, 598.
Office Action dated Sep. 4, 2018, issued on the corresponding Japanese patent application No. 2018-535907 with English translation.
Extended European Search Report dated Sep. 9, 2020, issued in the corresponding European Patent application No. 17882672.3.
Office Action dated Mar. 3, 2022, issued in the corresponding Chinese patent application No. 201780079488.3 with English translation.
Office Action issued in Korean Patent Application No. KR 10-2019-7014084, dated Jun. 13, 2022, with English Translation.
Office Action issued in corresponding Chinese Patent Application No. CN 201780079488.3, dated Sep. 28, 2022.

* cited by examiner

CELL CULTURE SUBSTRATE

TECHNICAL FIELD

The present invention relates to a substrate for use in cell culture.

BACKGROUND ART

Human pluripotent stem cells such as human iPS cells or ES cells have attracted much attention, in view of the applicability to pathological elucidation, new drug development, and regenerative medicine. For the utilization of human pluripotent stem cells, it is necessary to culture the cells stably and safely, and it is also necessary to apply, after the cultured cells are harvested, the harvested cells to drug discovery or medical treatment.

Conventionally, low culture rates have been a problem for human pluripotent stem cells. As one of the solutions, a culturing method of utilizing feeder cells has been attempted; however, since there is a problem that feeder cells that have been used cause contamination, it cannot be said that the method is safe.

As countermeasures for that, it has been reported in PTL 1 that human pluripotent stem cells can be cultured even in a feeder cell-free manner, by applying laminin and laminin fragments, which are extracellular matrices, on a cell culture substrate.

Meanwhile, according to PTL 1, culturing on the substrate is possible; however, nothing is mentioned about the harvest of cultured cells, and there still is a problem in view of saying that cultured cells are utilized. For example, since cells cultured by the above-described method have strong adhesion to the extracellular matrices, cells are harvested by a method of enzymatically treating the cells and then physically scraping the cells with a cell scraper (spatula made of rubber or a resin) or the like. Thus, from the viewpoint that the operation efficiency is low and cells are physically stimulated, there is a problem that the method adversely affects the survival rate of cells.

On the other hand, on the occasion of utilizing the extracellular matrices such as laminin for human pluripotent stem cells, there is a problem that the extracellular matrices are likely to be deactivated. Particularly, when the substrate surface is dry, the extracellular matrices are deactivated, and the culture efficiency of human pluripotent stem cells is decreased. When storage, transportation, and the like of a cell culture substrate are considered, it is important to maintain the culture efficiency even in a dry state. In PTL 2, a cell culture substrate that is coated with proteins other than laminin and can thereby withstand a dry state, is disclosed; however, although culturing is also made possible in this way, the problem with the harvest of cultured cells is not addressed.

CITATION LIST

Patent Literature

PTL 1: WO 2011/043405
PTL 2: WO 2014/199754

SUMMARY OF INVENTION

Technical Problem

It is an object of the present invention to provide a cell culture substrate, with which even human pluripotent stem cells can be cultured with high efficiency and the cells obtained after culturing can be detached and harvested while maintaining a high survival rate. Furthermore, another object of the invention is to provide a cell culture substrate that allows cell detachment and can withstand even a dry state.

Solution to Problem

The inventors of the present invention have conducted a thorough investigation, and as a result, the inventors found that a cell culture substrate including: a polymer having a lower critical solution temperature; one or more inorganic materials selected from a water-swellable clay mineral and silica; and an adhesive matrix, in which the adhesive matrix is an extracellular matrix and/or an adhesive synthetic matrix, can solve the problems described above.

Furthermore, there is provided a cell culture substrate in which the extracellular matrix is at least one selected from laminin, fibronectin, vitronectin, cadherin, and fragments thereof.

Furthermore, there is provided a cell culture substrate in which the adhesive synthetic matrix is poly[2-(methacryloyloxy)ethyl dimethyl-(3-sulfopropyl) ammonium hydroxide] or an oligopeptide-supporting polymer.

There is provided a cell culture substrate in which the polymer having a lower critical solution temperature is at least one of:

a copolymer (B1) of a monomer (a) represented by the following Formula (1) and a hydrophilic amide-based vinyl monomer (b), a copolymer (B2) of the monomer (a) and a monomer (c) represented by the following Formula (2), or a copolymer (B3) of monomer (a) and a polyethylene glycol chain-containing monomer (d) represented by the following Formula (3), in which the percentage content of the polymer having a lower critical solution temperature with respect to the total amount of the cell culture substrate is 5% by mass to 99% by mass.

[Chem. 1]

wherein $R_1$ represents a hydrogen atom or a methyl group; $R_2$ represents an alkylene group having 2 or 3 carbon atoms; and $R_3$ represents an alkyl group having 1 or 2 carbon atoms.

[Chem. 2]

where $R_4$ represents a hydrogen atom or a methyl group; and $R_5$ represents an alkylene group having 2 or 3 carbon atoms.

[Chem. 3]

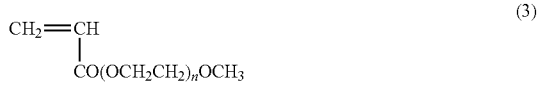

wherein n represents an integer of 2 to 20.

Furthermore, there is provided a cell culture substrate in which the water-swellable clay mineral is one or more clay minerals that delaminate into 1 to 10 layers in an aqueous medium (W), the water-swellable clay mineral being selected from water-swellable hectorite, water-swellable montmorillonite, water-swellable saponite, and water-swellable synthetic mica, and the silica is water-dispersible colloidal silica.

Furthermore, there is provided a cell culture substrate containing a polymer having a lower critical solution temperature further includes thereon at least one protein selected from gelatin, collagen, and/or albumin.

Furthermore, there is provided a method for producing a dry cell culture substrate, the method including:

a step of applying a solution including at least one protein selected from gelatin, collagen, and/or albumin on a polymer having a lower critical solution temperature;

a step of further applying a solution including the adhesive matrix mentioned above thereon to obtain a cell culture substrate; and a step of drying the obtained cell culture substrate.

Advantageous Effects of Invention

The cell culture substrate of the present invention allows human pluripotent stem cells to be cultured with high efficiency, and the cells obtained after culturing can be detached and harvested from the substrate with a high survival rate.

Furthermore, a substrate that enables, even after going through a dry state, cell culture and also enables cell detachment is disclosed.

DESCRIPTION OF EMBODIMENTS

The present invention provides a cell culture substrate comprising a polymer having a lower critical solution temperature, the substrate comprising one or more inorganic materials selected from a water-swellable clay mineral and silica and further including an adhesive matrix on the substrate, in which the adhesive matrix is an extracellular matrix and/or an adhesive synthetic matrix.

Polymer Having Lower Critical Solution Temperature

A polymer having a lower critical solution temperature according to the present invention is a polymer that dissolves in water when the temperature reaches a certain temperature or lower. Examples of the polymer having a lower critical solution temperature include the following 1) and 2).

1) A homopolymer having a lower critical solution temperature by polymerizing.

2) A copolymer of a hydrophobized monomer and a hydrophilic monomer.

The polymer 1) is a homopolymer by polymerizing only a monomer that gives a homopolymer having a lower critical solution temperature. Examples of the monomer that gives a homopolymer having a lower critical solution temperature include N-isopropyl (meth)acrylamide, N-n-propyl (meth)acrylamide, N-cyclopropyl (meth)acrylamide, N-ethoxyethyl (meth)acrylamide, N-tetrahydrofurfuryl (meth)acrylamide, N-ethylacrylamide, N-ethyl-N-methylacrylamide, N,N-diethylacrylamide, N-methyl-N-n-propylacrylamide, N-methyl-N-isopropylacrylamide, N-acryloylpiperidine, and N-acryloylpyrrolidine. These monomers may be utilized singly, or a plurality of kinds thereof may be utilized simultaneously.

The homopolymer by polymerizing a monomer that gives a homopolymer having a lower critical solution temperature according to 1) can conveniently produce a polymer having a lower critical solution temperature. However, there is a problem that these monomers have low adhesiveness to plastic surfaces and when brought into contact with water, an coated polymer layer is easily detachable. However, since the cell culture substrate of the present invention contains inorganic materials such as a water-swellable clay mineral and silica, a three-dimensional network structure is formed between the polymer and the inorganic material by ionic bonding or hydrogen bonding, and excellent water resistance is obtained. Therefore, the cell culture substrate can be used without detachment.

The copolymer 2) is a copolymer of a hydrophobized monomer and a hydrophilic monomer. In order for a copolymer of a hydrophobized monomer and a hydrophilic monomer to have a lower critical solution temperature, examples include:

2-1) a case in which the hydrophilic monomer is a monomer that gives a homopolymer having a lower critical solution temperature as described above; and 2-2) a copolymer (B1) of a monomer (a) represented by the following Formula (1) and a hydrophilic amide-based vinyl monomer (b), a copolymer (B2) of the monomer (a) and monomer (c) represented by the following Formula (2), or a copolymer (B3) of monomer (a) and a polyethylene glycol chain-containing monomer (d) represented by the following Formula (3).

[Chem. 4]

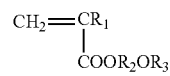

(1)

wherein $R_1$ represents a hydrogen atom or a methyl group; $R_2$ represents an alkylene group having 2 or 3 carbon atoms; and $R_3$ represents an alkyl group having 1 or 2 carbon atoms.

[Chem. 5]

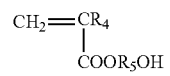

(2)

wherein $R_4$ represents a hydrogen atom or a methyl group; and $R_5$ represents an alkylene group having 2 or 3 carbon atoms.

[Chem. 6]

(3)

wherein n represents an integer of 2 to 20.

A hydrophobized monomer is a monomer that is water-soluble originally but becomes insoluble in an aqueous solvent when polymerized. In a case in which such a monomer is included in a copolymer, a cell culture substrate that has excellent water resistance and is not easily detachable from the supporting medium, can be obtained.

Regarding the hydrophobized monomer, a compound represented by Formula (1), diacetone acrylamide, polypropylene glycol (meth)acrylate, methoxy diethylene glycol acrylate, and methoxy triethylene glycol acrylate may be mentioned. These may be used singly, or a plurality of kinds thereof may be used simultaneously. Among them, 2-methoxyethyl acrylate, 2-ethoxyethyl acrylate, and 3-methoxypropyl acrylate are preferred, and 2-methoxyethyl acrylate and 2-ethoxyethyl acrylate are particularly preferred.

In the case of the copolymer disclosed in 2-2), the lower critical solution temperature of the copolymer thus obtainable can be widely controlled by the types or ratio of the monomers. Furthermore, by changing the types or ratio of the monomers according to the type of cells, the copolymer acquires more satisfactory cell adhesiveness and proliferation properties, and cells can be cultured, which is preferable. For example, as the ratio of monomer (b or c or d) is increased with respect to monomer (a), the lower critical solution temperature of the copolymer thus obtainable is shifted toward the higher temperature side. This ratio and the lower critical solution temperature are in an almost linear relationship. Since the cell culture temperature is usually 37° C., it is preferable to prepare the copolymer such that the lower critical solution temperature of the copolymer thus obtainable is near 20° C. to 32° C.

Inorganic Material

The inorganic material of the present invention is one or more inorganic materials selected from a water-swellable clay mineral and silica. The water-swellable clay mineral may be a water-swellable clay mineral that can be peeled into a lamellar form, and preferably, a clay mineral that can swell in water or a mixed solution of water and an organic solvent and can be uniformly dispersed, and particularly preferably an inorganic clay mineral that can be uniformly dispersed in water into a molecular form (monolayer) or a level close thereto, is used. Specifically, examples include water-swellable hectorite that includes sodium as an intercalated ion, water-swellable montmorillonite, water-swellable saponite, and water-swellable synthetic mica. These clay minerals may be used as mixtures.

Regarding the silica ($SiO_2$) to be used for the present invention, colloidal silica may be mentioned, and preferably, a colloidal silica that can be uniformly dispersed in an aqueous solution and has a particle size of 10 nm to 500 nm, and particularly preferably a colloidal silica having a particle size of 10 to 50 nm, is used.

By incorporating the inorganic material of the present invention, water resistance is enhanced, and the adhesiveness to a supporting medium is enhanced. Furthermore, the polymer having a lower critical solution temperature and the inorganic material of the present invention are bonded non covalently by interacting with each other mainly by ionic bonding, hydrogen bonding, or the like. This bonding force is strong, and the polymer and the inorganic material cannot be easily separated. Due to the interaction, even when exposed to sterilizing radiation (γ-radiation, electron beam), the polymer is not easily crosslinked, and therefore, the polymer has radiation-resistant sterilizing properties.

Polymer (A) of Monomer (a)

The cell culture substrate of the present invention may further include a polymer (A) of the monomer (a). By including the polymer (A), water resistance of the cell culture substrate is enhanced.

Production Method

Next, the production method of the present invention will be described.

The production method is a method for producing a cell culture substrate, the method comprising carrying out the following in sequence:

step 1 of mixing the above-mentioned monomer (a), the above-mentioned inorganic material (C), and a polymerization initiator (D) in an aqueous medium (W) such that the concentration of the inorganic material (C) of the present invention in the aqueous medium (W) is in the range represented by the following Formula (4) or Formula (5), subsequently polymerizing the monomer (a), and thereby producing a dispersion liquid ($L_{MC}$) of a composite ($X_{MC}$ of a polymer (A) and the inorganic material (C); and step 2 of adding the above-mentioned polymer (B) to the dispersion liquid (L), uniformly mixing the mixture, coating the mixture on a supporting medium, and then drying the mixture. Formula (4) When Ra<0.19, Concentration (mass %) of inorganic material
   $(C)<12.4Ra+0.05$ Formula (5) When Ra≥0.19, Concentration (mass %) of inorganic material
   $(C)<0.87Ra+2.17$ wherein the concentration (mass %) of the inorganic material (C) is a value obtained by dividing the mass of the inorganic material (C) by the total mass of the aqueous medium (W) and the inorganic material (C) and multiplying the resultant by 100; and Ra represents the mass ratio ((C)/(A)) between the inorganic material (C) and the polymer (A).

Regarding the monomer (a), inorganic material (C), and polymer (B) that are used for this production method, since the same materials as those mentioned in the explanation for the cell culture substrate can be used, no further explanation will be repeated here.

The aqueous medium (W) to be used for the production method of the present invention may be any aqueous medium which can include the monomer (a), the inorganic material (C), or the like, and with which an organic-inorganic composite dispersion liquid having favorable physical properties should be obtained by polymerization, and there are no particular limitations. For example, water or an aqueous solution including a solvent that is miscible with water and/or other compounds may be used, and an antiseptic agent, an antibacterial agent, a coloring material, a fragrance, an enzyme, a protein, collagen, a sugar, a peptide, an amino acid, a cell, a DNA, a salt, a water-soluble organic solvent, a surfactant, a polymer compound, a leveling agent, and the like can be included therein.

Regarding the polymerization initiator (D) to be used for the present invention, any known radical polymerization initiator can be selected as appropriate and used. Preferably, a polymerization initiator that is water-soluble or water-dispersible and is included uniformly in the entire system is preferably used. Specifically, examples of the polymerization initiator include water-soluble peroxides, for example, potassium peroxodisulfate and ammonium peroxodisulfate; water-soluble azo compounds, for example, VA-044, V-50, and V-501 (all manufactured by Wako Pure Chemical Industries, Ltd.); and a mixture of Fe2+ and hydrogen peroxide.

Regarding the catalyst, a tertiary amine compound such as N,N,N',N'-tetramethylethylenediamine is preferably used. However, it is not necessarily essential to use a catalyst. Regarding the polymerization temperature, for example, a temperature of 0° C. to 100° C. is used according to the type of the polymerization catalyst or the initiator. The polymerization time can also be adjusted to be between several dozen seconds and several dozen hours.

Meanwhile, a photopolymerization initiator is not easily affected by oxygen inhibition and has a fast polymerization rate, and therefore, a photopolymerization initiator is suitably used as the polymerization initiator (D). Specific examples include acetophenones such as p-tert-butyltrichloroacetophenone; benzophenones such as 4,4'-bisdimethylaminobenzophenone; ketones such as 2-methylthioxanthone; benzoin ethers such as benzoin methyl ether; α-hydroxyketones such as hydroxycyclohexyl phenyl ketone; phenylglyoxylates such as methyl benzoylformate; and metallocenes.

The photopolymerization initiators mentioned above are non-water-soluble. The term non-water-soluble as used herein means that the amount of the polymerization initiator soluble in water is 0.5% by mass or less. By using a non-water-soluble polymerization initiator, it is easier for the initiator to be present in the vicinity of the clay mineral, there is a larger number of initiation reaction points from the vicinity of the clay mineral, the particle size distribution of the composite (X) of the polymer (A) and the inorganic material (C) thus obtainable is narrow, and the dispersion liquid (L) has high stability. Thus, it is preferable.

It is preferable that a solution obtained by dissolving the photopolymerization initiator in a solvent (E) that is compatible with the aqueous medium (W) is added to the aqueous medium (W). The photopolymerization initiator can be dispersed more uniformly by this method, and a composite (X) having a more uniform particle size is obtained.

The mass ratio (D)/(E) of the photopolymerization initiator (D) and the solvent (E) in the solution obtained by dissolving the photopolymerization initiator (D) in the solvent (E) is preferably 0.001 to 0.1, and more preferably 0.01 to 0.05. When the mass ratio is 0.001 or more, a sufficient amount of radicals generated by irradiation with ultraviolet radiation is obtainable, and therefore, the polymerization reaction can be carried out suitably. When the mass ratio is 0.1 or less, there is no substantially occurrence of color development or foul odor caused by the initiator, and the production cost can be reduced.

Regarding the solvent (E) of the present invention, any solvent that is capable of dissolving the photopolymerization initiator (D) and the non-water-soluble polymerization initiator (D) and is water-soluble to or above a certain level can be used. The solvent that is water-soluble as used herein is preferably a solvent that can dissolve in an amount of 50 g or more in 100 g of water. When the solubility in water is 50 g or more, the dispersibility of the non-water-soluble polymerization initiator (D) in the aqueous medium (W) is favorable, the particle size of the composite (X) thus obtainable more easily becomes uniform, and the dispersion liquid (L) acquires high stability. Thus, it is preferable.

Examples of the water-soluble solvent include amides such as dimethylacetamide and dimethylformamide; alcohols such as methanol, ethanol, and 2-propanol; dimethyl sulfoxide; and tetrahydrofuran. These solvents may also be used as mixtures It is preferable that the amount of addition of the solution obtained by dissolving the photopolymerization initiator (D) in the solvent (E) is 0.1% by mass to 5% by mass, and more preferably 0.2% by mass to 2% by mass, with respect to the total mass of the monomer (a), inorganic material (C), aqueous medium (W), polymerization initiator (D), and solvent (E). When the dispersed amount is 0.1% by mass or more, polymerization is initiated sufficiently. When the dispersed amount is 5% by mass or less, problems such as the generation of foul odor caused by an increase in the amount of the polymerization initiator in the composite (X), and re-aggregation of the photopolymerization initiator that has been once dispersed, can be reduced, and a uniform dispersion liquid (L) of the composite (X) is obtained. Therefore, it is preferable.

It is a feature of the method for producing a cell culture substrate of the present invention that the concentration (mass %) of the inorganic material (C) in the aqueous medium is in the range represented by Formula (4) or Formula (5). When the concentration (mass %) of the inorganic material (C) in the aqueous medium is in the above-described range, a satisfactory dispersion liquid (L) of the composite (X) is obtained, application of the dispersion liquid on a supporting medium is made easy, and a thin coating film that is smooth and uniform is obtained. Thus, it is preferable.

The dispersion liquid (L) produced by the production method of the present invention may be used directly, or may be used after being subjected to a purification process carried out by washing with water or the like. Furthermore, it is also acceptable to use the dispersion liquid (L) after a leveling agent, a surfactant, a peptide, a protein, collagen, an amino acid, a peptide, a polysaccharide, a polymer compound, and the like are further added thereto.

Regarding the light sources for the polymerization that are used for the first step of the present production method are an electron beam, γ-radiation, X-radiation, ultraviolet light, visible light, and the like can be used; however, above all, it is preferable to use ultraviolet light from the viewpoints of the apparatus and the convenience of handling. The intensity of the ultraviolet light to be irradiated is preferably 10 to 500 mW/cm$^2$, and the irradiation time is generally about 0.1 seconds to 200 seconds. In conventional thermal radical polymerization, oxygen works as an inhibitor for polymerization; however, in the present invention, it is not necessarily essential to perform preparation of solutions and polymerization brought by ultraviolet irradiation in an oxygen-blocked atmosphere, and these processes can be carried out in an air atmosphere. However, there are occasions in which the polymerization rate can be made faster by performing ultraviolet irradiation in an inert gas atmosphere, and thus it is desirable.

The application method that is used for step 2 of the present production method may be any conventionally known method, and examples thereof include a method of flow casting the dispersion liquid on a supporting medium; an application method using a bar coater or a spin coater; and a spraying method such as spraying. Furthermore, in a case in which the dispersion liquid patternwise, a method of coating the dispersion liquid on a rubber plate having a pattern and then transferring the dispersion liquid onto a supporting medium; a method of masking in advance a supporting medium in the areas where the dispersion liquid will not be applied, applying the dispersion liquid, and then removing the masked parts; and a method of coating the dispersion liquid by an inkjet printer method, may be used.

Regarding the drying method, any method may be employed as long as volatile components in the dispersion liquid (L) are volatilized, and a thin layer of the composite (X) is produced. Examples include natural drying at room temperature, drying by room temperature air blowing, heating, or hot air, and drying by far-infrared radiation. Alternatively, a method of blowing hot air or heating the dispersion liquid while rotating the dispersion liquid with a spin coater may also be used.

With regard to the polymer (B) used in the present production method, the weight average molecular weight Mw is preferably $1\times10^4$ to $2\times10^7$, and more preferably $1\times10^5$ to $5\times10^6$. When the weight average molecular weight is $1\times10^4$ or more, sufficient cell detachment properties can be maintained, and when the weight average molecular weight is $2\times10^7$ or less, sufficient cell proliferability can be maintained. Thus, a cell culture substrate having superior performance can be produced.

The present production method has a feature that the rate of proliferation of cells can be widely adjusted by adjusting the ratio of the monomer (a) and the inorganic material (C), and the rate of detachment of cells caused by temperature change can be controlled by adjusting the type or the lower critical solution temperature and the content of the polymer (B).

The surface of the cell culture substrate obtained by the present production method is not covered by a layer of a polymer (B), but has a structure in which the polymer (B) grows out from a thin layer of the composite (X), and the surface of the thin layer is also adequately exposed. The polymer (B) is bonded to the clay mineral or silica by ionic bonding, hydrogen bonding, or the like from the interior of the thin layer of the composite (X) to the surface, and a stable structure is formed without having the bonding broken by a physical force or even in water.

Furthermore, as a second production method of the present invention, the following method may be mentioned. That is, a method for producing a cell culture substrate may be mentioned, the method including step 1 of producing a dispersion liquid ($L_{NC}$) of a composite ($X_{MC}$) of a polymer (B) having a lower critical solution temperature and the inorganic material (C) by mixing monomers that give, when polymerized, a polymer having a lower critical solution temperature (for example, a combination of (a) and (b), a combination of (a) and (c), a combination of (a) and (d), or a monomer (e) that gives a homopolymer having a lower critical solution temperature), the inorganic material (C), and a polymerization initiator (D) into an aqueous medium (W) such that the concentration of the inorganic material (C) in the aqueous medium (W) is in the range represented by the following Formula (4) or Formula (5), and then polymerizing the monomers; and step 2 of coating the dispersion liquid ($L_{MC}$) on a supporting medium and then drying the dispersion liquid.

Regarding the monomers (a), (b), (c), (d), and (e), the inorganic material (C), and the polymer (B) that are used for this second production method, the same materials as those described in the explanation of the cell culture substrate can be used, and therefore, further explanation will not be repeated here. Furthermore, the method for polymerizing the dispersion liquid or the method for producing the substrate are similar to the first production method, and therefore, further explanation will not be repeated here.

A cell culture substrate obtained by the present second production method has a stable structure in which a polymer (B) having a lower critical solution temperature and an inorganic material are stacked in a lamellar form, and the polymer (B) and the inorganic material are bonded by ionic bonding, hydrogen bonding, or the like, without having the bonding broken by a physical force or even in water.

Furthermore, it is speculated that the surface is covered with a thick layer of the polymer (B), so that in a case in which the cell culture substrate is subjected to a temperature change from a temperature higher than the lower critical solution temperature to a temperature lower than the lower critical solution temperature in an aqueous solution, there occurs a movement by which the molecules of the polymer (B) grow large, and high cell detachability is obtained.

Adhesive Matrix

The cell culture substrate of the present invention includes an adhesive matrix in the substrate, and examples of the adhesive matrix with which the culturing performance for human pluripotent stem cells is enhanced include an extracellular matrix and an adhesive synthetic matrix.

Specific examples of the extracellular matrix include laminin, fibronectin, vitronectin, cadherin, and fragments thereof. Preferred examples include laminin, vitronectin, and fragments thereof. Regarding the extracellular matrix, any animal-derived extracellular matrix can be utilized; however, human- and mouse-derived extracellular matrices are preferred. More preferred are extracellular matrices produced as recombinant proteins. As commercially available products, Matrigel (manufactured by Corning, Inc.), Geltrex (manufactured by Thermo Fisher Scientific, Inc.), iMatrix-511 (manufactured by Nippi, Inc.), Laminin 521 (BioLamina AB), and the like can be utilized.

Simultaneously with the extracellular matrix, a Rho-associated coiled-coil kinase (ROCK) inhibitor may be used. By using a ROCK inhibitor, culture of human pluripotent stem cells dispersed into single cells is further facilitated. Examples of the ROCK inhibitor include Y-27632 (Wako Pure Chemical Industries, Ltd.) and Fasudil hydrochloride (manufactured by Tokyo Chemical Industry Co., Ltd.).

The adhesive synthetic matrix may be poly[2-(methacryloyloxy)ethyl dimethyl-(3-sulfopropyl) ammonium hydroxide] (hereinafter, abbreviated to PMEDSAH) or an oligopeptide-supporting polymer. The oligopeptide-supporting polymer is a matrix obtained by covalently bonding an oligopeptide having an arginine-glycine-aspartic acid (RGD) sequence, which has cell adhesive activity, to a polymer. A commercially available product thereof may be Synthemax (manufactured by Corning, Inc.).

The adhesive matrix may be provided to the substrate by any method. For example, the adhesive substrate may be mixed into the substrate, or the adhesive substrate may be coated on the substrate. Furthermore, the adhesive substrate may be incorporated into a cell culture medium and may be provided in the form of being brought into contact with the substrate together with the medium.

This adhesive substrate may exist uniformly in the substrate or may exist non-uniformly. It is preferable in a case in which the adhesive matrix exists on the substrate surface. In a case in which the adhesive matrix is coated, regarding the coating method, a solution of the adhesive matrix may be applied using a conventionally known method, and the solution may be applied by spray coating, spin coating, inkjetting or the like, or may be stamped using a plate. A method of pouring the solution on the substrate, leaving the substrate to stand for a certain time period, and then removing the solution may also be used, and the application method may be selected as appropriate according to the method of use.

In the case of coating the adhesive matrix on the surface of the cell culture substrate, the coating amount is preferably 0.01 to 5 µg/cm$^2$, more preferably 0.2 to 2 µg/cm$^2$, and particularly preferably 0.5 to 1 µg/cm$^2$, per area of the cell culture substrate.

Other Admixtures

The cell culture substrate of the present invention may include admixtures in addition to the extracellular matrix, gelatin, or collagen. For example, an antiseptic agent, an antibacterial agent, a coloring material, a fragrance, an enzyme, a sugar, a protein, a peptide, an amino acid, a cell, a DNA, a salt, a water-soluble organic solvent, a surfactant, a polymer compound, a leveling agent, and the like may also be included.

Gelatin, Collagen, or Albumin

Furthermore, in order to maintain the activity of the adhesive matrix or to increase the cell culture efficiency, gelatin, collagen, or albumin may be caused to exist on the cell culture substrate. Gelatin, collagen, or albumin may be mixed into the cell culture substrate or may be coated thereon, similarly to the adhesive matrix. In the case of coating the material, it is preferable that gelatin, collagen, or albumin is coated first, and then the adhesive matrix is coated, from the viewpoint of maintaining the activity of the adhesive matrix or from the viewpoint of the cell culture efficiency. Furthermore, gelatin, collagen, or albumin may be used singly, or a plurality of kinds thereof may be used simultaneously.

The coating amount of gelatin, collagen, or albumin is preferably 0.5 to 500 µg/cm$^2$, more preferably 5 to 200 µg/cm$^2$, and particularly preferably 20 to 100 µg/cm$^2$.

Cell Culture Substrate

The shape of the cell culture substrate of the present invention is not particularly limited as long as cell culture can be achieved thereon, and cultured cells can be easily detached by a low temperature treatment. Examples include a film-shaped substrate, a dish-shaped substrate, a bottle-shaped substrate, a tube-shaped substrate, a thread-shaped or rod-shaped substrate having a thickness of 5 nm to 5 mm, a bag-shaped substrate, a multi-well plate-shaped substrate, a microflow channel-shaped substrate, a porous membrane-shaped or network-shaped substrate (for example, TRANSWELL or a cell strainer), and a spherical-shaped substrate having a particle size of preferably 10 to 2,000 µm, and more preferably 100 to 500 µm.

The cell culture substrate of the present invention may be used alone as a simple substance. Preferably, the cell culture substrate is used in the form of a cell culture equipment including a supporting medium and the substrate formed on the supporting medium. It is because in a case in which the cell culture substrate is used in the form of a cell culture equipment, excellent convenience in transportation, storage, and the like is obtained, and the cell culture substrate can also be used directly as a culture container or a carrier for culture.

The material of the supporting medium to be used for the present invention is not particularly limited as long as the culture substrate can be sufficiently adhered thereto, cell culture can occur on the culture substrate thus adhered, and cultured cells can be easily detached by a low temperature treatment. For example, a styrene-based resin such as polystyrene; a polyolefin-based resin such as polypropylene; a polyurethane-based resin; a polycarbonate; polyethylene terephthalate (PET); a polysulfone-based resin; a fluororesin; a polysaccharide natural polymer such as cellulose; an inorganic material such as glass or ceramic; and a metallic material such as stainless steel or titanium, are suitably used.

The shape of the supporting medium is not particularly limited, and any shape that can serve as a supporting medium of the cell culture substrate of the present invention is acceptable. Examples include a film-shaped supporting medium, a membrane-shaped supporting medium, a plate-shaped supporting medium, a spherical-shaped supporting medium, a polygonal-shaped supporting medium, a rod-shaped supporting medium, a dish-shaped supporting medium, a bottle-shaped supporting medium, a tubular-shaped supporting medium, a needle/thread-shaped supporting medium, a fiber-shaped supporting medium, a bag-shaped supporting medium, a multi-well plate-shaped supporting medium, a microflow channel-shaped supporting medium, a porous membrane-shaped supporting medium, and a network-shaped supporting medium (for example, TRANSWELL or a cell strainer). A shape combining these is acceptable, and an irregularly shaped supporting medium that does not have a particular shape is also acceptable.

Furthermore, the cell culture substrate of the present invention may be integrated with a supporting medium and used as a cell culture equipment, or the cell culture substrate may be detached from the supporting medium and used alone.

Dry Cell Culture Substrate

The cell culture substrate of the present invention enables culturing of human pluripotent stem cells even after a dry state. Therefore, since the cell culture substrate can withstand long-term storage or transportation, the cell culture substrate is highly industrially applicable.

The drying method is not particularly limited, and the cell culture substrate may be laminated on the supporting medium that will be described below and then dried. For example, room temperature drying (18° C. to 30° C., humidity 20% to 60% RH), heated drying (30° C. to 37° C.), and drying using a constant temperature dryer or a desiccators may be employed. From the viewpoint of preventing denaturation of proteins, room temperature drying is preferred.

The film thickness of the cell culture substrate at the time of drying is preferably 1,000 nm or less, and more preferably 500 nm or less. It is because when the film thickness is 1,000 nm or less, satisfactory cell culturing performance is obtained.

Cultured Cells

The cell culture substrate of the present invention enables suitable culturing of various cells, particularly animal cells. Regarding the animal cells, the origin may be any animal, and examples include human being, mouse, and monkey, while artificial cells are also acceptable. The type of cell is not particularly limited; however, examples include epithelial cells (corneal epithelial cells, and the like), endothelial cells (human umbilical vein endothelial cells, and the like), fibroblastic cells (human skin fibroblasts, mouse fibroblasts, and the like), blood corpuscles, contractile cells (skeletal muscle cells, cardiac muscle cells, and the like), blood and immune cells (red blood corpuscles, macrophages, and the like), nerve cells (neurons, glial cells, and the like), pigment cells (retinal pigment cells, and the like), liver cells, cartilage cells, osteoblastic cells, and stem cells (ES cells, iPS cells, hematopoietic stem cells, skin stem cells, germ stem cells, EC cells, EG cells, and neural stem cells). Among them, the cell culture substrate of the present invention can be suitably utilized for stem cells that are difficult to culture, particularly ES cells and iPS cells.

Method for Culturing Cells

Regarding the culturing method, any conventionally known method may be used. For example, a predetermined amount of a medium or a culture reagent is introduced into a culture substrate formed on the bottom surface of a dish-shaped container, cells are inoculated therein, and the cells may be cultured under predetermined temperature and $CO_2$ concentration conditions, or a culture substrate formed into a filamentous form or a spherical form is introduced into a commercially available polystyrene container containing a medium, and cells may be inoculated and cultured therein. In the latter case, the cells do not adhere to the polystyrene container but adhere to the surface of the filamentous or spherical culture substrate and proliferate. For example, in a case in which a filamentous culture substrate having a thickness of 50 μm is used, since the cells grow in the longitudinal direction of a filament, the cells may be cultured in a form having a controlled cell shape. Furthermore, in the case of using a spherical culture substrate, there is an advantage that the culture substrate has a larger surface area and can culture more cells, compared to conventional dish-shaped containers.

Method for Detaching Cells (Temperature Control Method)

The method for detaching cultured cells from the substrate is not particularly limited; however, for example, after completion of culturing, the medium at 37° C. is replaced with a medium at a predetermined temperature (6° C. to 30° C.), the system is left to stand at a predetermined temperature (6° C. to 30° C.), and natural detachment of cells may be waited for. Alternatively, cells may be detached by physically stimulating the cells by lightly agitating the culture container, by a "pipetting" operation of sucking in and out the medium with a pipette, or with a mild water stream.

Method for Detaching Cells (Enzymatic Method)

In a case in which it is wished to break binding between cells and obtain individual single cells, a detachment method based on an enzymatic treatment may be used. The type of the protease to be used may be selected as appropriate according to the type of the cells. Examples include trypsin, trypsin/EDTA, and TrypLE Select (Thermo Fisher Scientific, Inc.). The treatment temperature or time may be adjusted as appropriate by the type of cells or the adhesive force to the substrate. For example, a method of removing the medium after completion of culturing, washing cells with a buffer solution or the like, adding an enzyme solution, leaving the system to stand for a certain time at 37° C., subsequently removing the enzyme solution, adding a buffer solution or a medium at a predetermined temperature (6° C. to 37° C.), and detaching the cells by standing or a "pipetting" operation, may be mentioned. Of course, the cells may also be detached by combining a low temperature treatment and the use of enzymes.

EXAMPLES

Hereinafter, the present invention will be specifically described by way of Examples; however, the scope of the present invention is not intended to be limited to these Examples.

GPC

The measurement method for GPC is as follows.
Apparatus: SHODEX GPC SYSTEM-21 (manufactured by Showa Denko K.K.)
Solvent: N,N-dimethylformamide (DMF) solution (containing 10 mmol/L LiBr)
Column: Two KF-705L columns connected
Standard substance: Polystyrene standard SH-75, SM-105 Kit (manufactured by Showa Denko K.K.)

Viscosity

The viscosity of a resin solution was measured with the following apparatus.
DIGITAL VISCOMATE viscometer (Model VM-100A, manufactured by YAMAICHI ELECTRONICS CO., LTD.)

Method for Measuring Lower Critical Solution Temperature (LCST)

The transmittance of a resin solution was measured under the following conditions, and the temperature at the inflection point was designated as the lower critical solution temperature (LCST).
Apparatus: Ultraviolet-visible spectrophotometer (V-530, manufactured by JASCO Corporation)
Wavelength: 600 nm (transmittance)
Temperature range: 25° C. to 40° C.
Rate of temperature increase: 10° C./60 min (Synthesis Example 1) (MC114)

Adjustment of Solution Having Polymerization Initiator (D) Dissolved in Solvent (E)

9.8 g of methanol as the solvent (E) and 0.2 g of 1-hydroxycyclohexyl phenyl ketone "IRGACURE 184" (manufactured by Ciba-Geigy AG) as the polymerization initiator (D) were uniformly mixed, and thereby solution (DE) was prepared.

Preparation of Aqueous Solution of Polymer (B)

2.3 g of N-isopropylacrylamide (manufactured by Kohjin Co., Ltd.) as a monomer, 100 g of water, 2 mL of a 2 mass % aqueous solution of potassium persulfate as a polymerization initiator, and 80 μL of N,N,N',N'-tetramethylethylenediamine as a catalyst were mixed, and then the mixture was left to stand for 15 hours at room temperature (20° C. to 28° C.). Thereby, an aqueous solution (AqB) of poly-N-isopropylacrylamide (PNIPA) was prepared. The viscosity of this solution was 19.6 mPa·s, and the solution temperature at the time of measurement was 25.7° C.
Furthermore, the weight average molecular weight Mw of this PNIPA was $3.40 \times 10^6$.

Preparation of Reaction Solution Including Monomer (a), Inorganic Material (C), and Aqueous Medium (W)

0.32 g of 2-methoxyethyl acrylate (manufactured by TOAGOSEI CO., LTD.) as the monomer (a), 0.02 g of a water-swellable clay mineral, LAPONITE XLG (manufactured by Rockwood Additives Ltd.) as the inorganic material (C), 10 g of water as the aqueous medium (W), and 50 µL of the solution (DE) as an initiator were uniformly mixed, and thereby reaction solution (1) was prepared.

Preparation of Dispersion Liquid (L) of Composite (X)

The reaction solution (1) was irradiated for 180 second with ultraviolet radiation having a wavelength of 365 nm at an ultraviolet intensity of 40 mW/cm$^2$, and thus a milky-white dispersion liquid (L1) of composite (X) was produced.

Ra of this reaction system=0.06, concentration (mass %) of inorganic material (C)=0.20(%)<12.4Ra+0.05=0.79

Preparation of Coating Liquid 3.12 g (solid content 0.07 g) of the aqueous solution of PNIPA (AqB) was introduced into the entire amount of the dispersion liquid (L1), the mixture was uniformly mixed, and thereby coating liquid 1 (MC114) was obtained.

The percentage content of the polymer having a lower critical solution temperature, PNIPA, with respect to the total amount of the cell culture substrate was 17% by mass.

(Synthesis Example 2) (MC414)

Coating liquid 2 (MC414) was prepared in the same manner as in Synthesis Example 1, except that 0.02 g of water-swellable clay mineral LAPONITE XLG as the inorganic material (C) of Synthesis Example 1 was changed to 0.08 g.

Ra of this reaction system=0.25, concentration (mass %) of inorganic material (C)=0.79(%)<0.87Ra+2.17=2.39

The percentage content of the polymer having a lower critical solution temperature, PNIPA, with respect to the total amount of the cell culture substrate was 15% by mass.

(Synthesis Example 3) (MC814)

Coating liquid 3 (MC814) was prepared in the same manner as in Synthesis Example 1, except that 0.02 g of water-swellable clay mineral LAPONITE XLG as the inorganic material (C) of Synthesis Example 1 was changed to 0.16 g.

Ra of this reaction system=0.5, concentration (mass %) of inorganic material (C)=1.57(%)<0.87Ra+2.17=2.61

The percentage content of the polymer having a lower critical solution temperature, PNIPA, with respect to the total amount of the cell culture substrate was 13% by mass.

(Synthesis Example 4) (NC214)

Preparation of Reaction Solution Including Monomer (a), Inorganic Material (C), and Aqueous Medium (W)

0.28 g of N-isopropylacrylamide as a monomer, 0.04 g of water-swellable clay mineral LAPONITE XLG as the inorganic material (C), 10 g of water as the aqueous medium (W), and 50 µL of the solution (DE) as an initiator were uniformly mixed, and thereby reaction solution (4) was prepared.

Preparation of Coating Liquid

While the periphery of a glass container holding the reaction solution (4) was cooled (about 10° C.), the reaction solution (4) was irradiated for 180 seconds with ultraviolet radiation having a wavelength of 365 nm at an ultraviolet intensity of 40 mW/cm$^2$, and thus coating liquid 4 (NC214), which was a milky-white dispersion liquid (L4) of composite (X), was produced.

Ra of this reaction system 32 0.14, concentration (mass %) of inorganic material (C)=0.40(%)<12.4Ra+0.05=1.79

The percentage content of the polymer having a lower critical solution temperature, PNIPA, with respect to the total amount of the cell culture substrate was 88% by mass.

TABLE 1

| Type of material | Synthesis Example 1 (MC114) | Synthesis Example 2 (MC414) | Synthesis Example 3 (MC814) | Synthesis Example 4 (NC214) |
|---|---|---|---|---|
| Monomer | MEA NIPA | MEA NIPA | MEA NIPA | — NIPA |
| Inorganic material | Clay | Clay | Clay | Clay |
| Polymerization initiator | Irg184 | Irg184 | Irg184 | Irg184 |
| Solvent | Water | Water | Water | Water |
| LCST (° C.) | 32 | 32 | 32 | 32 |

MEA: 2-Methoxyethyl acrylate
NIPA: N-isopropylacrylamide
Irg184: IRGACURE 184

Example of Alkaline Phosphatase Staining (AP Staining)

Since undifferentiated iPS cells exhibit high alkaline phosphatase activity, they are stained dark. In contrast, differentiated cells do not exhibit alkaline phosphatase activity and are not stained.

As a reagent, "Leukocyte Alkaline Phosphatase Kit" manufactured by Sigma-Aldrich Corp. was used. Regarding the operation procedure, after completion of culture, the medium in the Petri dish is removed, a PBS (phosphate buffer solution) is added thereto, cells are washed, and then the PBS is removed. Next, a fixing solution is added thereto, the system is left to stand for about one minute, and then the fixing solution is removed. The cells are washed with water, subsequently a stain solution is added thereto, and the mixture is left to stand for one hour at room temperature (25° C.). The stain solution is removed, the cells are washed with water, amounting agent is introduced, and the cells are covered with a cover glass and are observed with a microscope. In a case in which the cells exhibit alkaline phosphatase activity (positive), the cells are stained red.

Detachment Rate and Survival Rate of Cells, and Measurement of Culturing Performance After completion of culture, a cell detachment operation is carried out by a temperature control method or an enzymatic method, and a suspension of the detached cells is suctioned into a cassette for exclusive use in cell measurement. The number of dead cells among the detached cells in the cell suspension is counted using a cell counting apparatus, NC-100 (manufactured by M&S TechnoSystems, Inc.). Furthermore, 100 µL of the detached cells is transferred into each medium in a 1.5-ml tube, and 100 µl each of Reagent A and Reagent B (manufactured by M&S TechnoSystems, Inc.) are added thereto. The mixture is uniformly mixed up by pipetting several times, and then similarly, the liquid is suctioned into a new cassette and is mounted in a cell counting apparatus, NC-100. Thus, the number of detached cells is counted. Furthermore, an appropriate amount of Reagent A is added to the Petri dish, from which all of detached cells after the detachment operation have been removed, and the Petri dish is left to stand for 10 minutes at room temperature (25° C.). Any cells remaining in the Petri dish are completely detached and dissolved using a scraper (rubber spatula), and then an appropriate amount of Reagent B is added thereto. The mixture is uniformly mixed up by pipetting several times and is mounted in a cell counting apparatus, NC-100. The number of undetached cells remaining in the Petri dish is counted. The cell detachment rate and survival rate, and culturing performance are calculated by the following Formulae (6), (7), and (8), respectively.

Detachment rate=[Number of detached cells/(number of detached cells+number of undetached cells)]×100   (6)

Survival rate=(1−number of dead cells among detached cells/number of detached cells)×100   (7)

Culturing performance=Total number of cells obtained with culture substrate/total number of cells obtained with TCPS (commercially available Petri dish for tissue culture)*   (8)

*Total number of cells=Number of detached cells+ number of undetached cells

Example 1

This is an example of sequentially coating collagen, laminin, and a ROCK inhibitor on the surface of a cell culture substrate, drying the culture substrate, and then evaluating the culture substrate with ReproFF2 medium.

Production of Culture Substrate

An appropriate amount of coating liquid 1 (MC114) prepared in Synthesis Example 1 was introduced into a 35-mm Petri dish made of polystyrene (TCPS, 35 mm/Tissue Culture Dish, manufactured by AGC Techno Glass Co., Ltd.), and the solution was thinly coated on the surface of the Petri dish using a spin coater. The Petri dish was dried for 20 minutes in a thermostat at 80° C. Next, the Petri dish was washed with sterilized water, and then the Petri dish was dried for 5 hours at 40° C. in a sterile bag. Thus, the cell culture substrate 1 (MC114) was obtained. The thickness of the coating film was measured using an AFM (atomic force microscope, manufactured by Bruker AXS, Inc., NanoScope® IIIa, measurement mode: DFM, average of two sites of sample measurement), and the film thickness was about 20 nm.

Coating of Adhesive Matrix

500 μL (equivalent to a coating amount of 50 μg/cm$^2$) of an aqueous solution of collagen (trade name: Cellmatrix Type I-C, manufactured by Nitta Gelatin, Inc.) at a concentration of 1 mg/ml was introduced into the cell culture substrate 1 (MC114), the mixture was left to stand for one hour at 37° C. Subsequently, the aqueous solution was discarded, and then 500 μL (equivalent to a coating amount of 0.05 μg/cm$^2$) of an aqueous solution of laminin (trade name: iMatrix, manufactured by Nippi, Inc.) at a concentration of 1 μg/mL was introduced therein. The mixture was left to stand for one hour at 37° C., and the aqueous solution was discarded. Furthermore, 500 μL (equivalent to a coating amount of 0.005 μmol/cm$^2$) of an aqueous solution of ROCK inhibitor Y-27632 (manufactured by Wako Pure Chemical Industries, Ltd.) at a concentration of 100 μmol/L was introduced therein, and the cell culture substrate was dried at room temperature of 25° C. (relative humidity 35% to 55% RH). Thus, culture container 1 was obtained.

Culture of iPS Cells and Evaluation of Detachment Rate 2 ml of ReproFF2 medium (manufactured by REPROCELL Inc.) was added to the culture container 1, and a certain amount (about 1×10$^4$ cells/cm$^2$) of human iPS cells (strain 201B7, manufactured by iPS Academia Japan, Inc.) were introduced into the culture container. The cells were left to stand in a thermostat at 37° C. in a 5% $CO_2$ atmosphere, and culture was carried out for 5 days. The medium was exchanged at a frequency of once in two days. Next, the cells were detached by a temperature control detachment method. That is, medium exchange was carried out with a cold medium at 4° C., and the cells were left to stand for 10 minutes at room temperature. Subsequently, a "pipetting operation" of sucking in and out the medium with a pipette was performed about 10 times, and thereby cell detachment was carried out. Next, the number of detached cells, the number of dead cells among the detached cells, and the total number of cultured cells were counted according to the method of "Detachment rate and survival rate of cells, and measurement of culturing performance", and the detachment rate, survival rate, and culturing performance were calculated by Formulae (6), (7), and (8).

Example 2

This is an example of increasing the amount of the inorganic material compared to Example 1.

Production of Culture Substrate

Cell culture substrate 2 (MC414) was formed on a Petri dish in the same manner as in Example 1, except that the coating liquid 2 (MC414) of Synthesis Example 2 was used instead of the coating liquid 1 (MC114) of Synthesis Example 1, and thus culture container 2 was produced. The thickness of the coating film was measured using AFM, and the film thickness was about 20 nm.

Furthermore, coating of the adhesive matrix, culture of iPS cells, and evaluation of the detachment rate were carried out in the same manner as in Example 1.

Example 3

This is an example of increasing the amount of the inorganic material compared to Example 1.

Production of Culture Substrate

Cell culture substrate 3 (MC814) was produced in the same manner as in Example 1, except that the coating liquid 3 (MC814) of Synthesis Example 3 was used instead of the coating liquid 1 (MC114) of Synthesis Example 1. The thickness of the coating film was measured using AFM, and the film thickness was about 20 nm.

Furthermore, coating of the adhesive matrix, culture of iPS cells, and evaluation of the detachment rate were carried out in the same manner as in Example 1.

Example 4

This is an example of coating collagen and laminin in sequence on the surface of the culture substrate 3, drying the culture substrate, and then evaluating the culture substrate with ReproFF2 medium.

Production of Culture Substrate

Cell culture substrate 3 (MC814), which is the same as that of Example 3, was used.

Coating of Adhesive Matrix

Collagen and laminin were coated in sequence on the surface of the culture substrate 3 in the same manner as in Example 1, and the culture substrate was subjected to drying without coating a ROCK inhibitor thereon.

Culture of iPS Cells and Evaluation of Detachment Rate

The detachment rate, survival rate, and culturing performance for iPS cells were evaluated in the same manner as in Example 1, except that a medium containing ROCK inhibitor Y27632 (amount of addition: 0.5 μg/mL of medium) added thereto was used instead of the ReproFF2 medium that was initially used, and that ReproFF2 medium containing ROCK inhibitor Y27632 (amount of addition: 0.5 μg/mL of medium) added thereto was used instead of the medium at the time of the first round of medium exchange.

Example 5

This is an example of coating laminin only on the surface of the culture substrate 3, drying the culture substrate, and then evaluating the culture substrate with StemFit Ak02N medium.

Production of Culture Substrate

Cell culture substrate 3 (MC814), which is the same as that of Example 3, was used.

Coating of Adhesive Matrix

Laminin was coated on the surface of the culture substrate 3 in the same manner as in Example 1, except that the collagen and the ROCK inhibitor used in Example 1 were not used, and an aqueous solution of laminin at a concentration of 10 μg/mL was used instead of the aqueous solution of laminin at a concentration of 1 μg/mL, and the culture substrate was subjected to drying.

Culture of iPS Cells and Evaluation of Detachment Rate

The detachment rate, survival rate, and culturing performance for iPS cells were evaluated in the same manner as in Example 1, except that StemFit Ak02N medium was used instead of the ReproFF2 medium of Example 1, and at the time of cell inoculation, StemFit Ak02N medium containing ROCK inhibitor Y27632 (amount of addition: 0.5 μg/mL of medium) added thereto was used instead of the medium.

Example 6

This is an example of coating laminin only on the surface of the culture substrate 4, drying the culture substrate, and then evaluating the culture substrate with StemFit Ak02N medium.

Production of Culture Substrate

Cell culture substrate 4 (NC214) was produced in the same manner as in Example 1, except that the coating liquid 4 (NC214) of Synthesis Example 4 was used instead of the coating liquid 1 (MC114) of Synthesis Example 1. The thickness of the coating film was measured using AFM, and the film thickness was about 30 nm.

Furthermore, coating of the adhesive matrix, culture of iPS cells, and evaluation of the detachment rate were carried out in the same manner as in Example 5.

Example 7

This is an example of coating a mixed liquid of laminin and gelatin on the surface of the culture substrate 4, drying the culture substrate, and then evaluating the culture substrate with StemFit Ak02N medium.

Coating of Adhesive Matrix

500 μL (equivalent to a gelatin coating amount of 10 μg/cm$^2$, equivalent to a laminin coating amount of 0.5 μg/cm$^2$) of an aqueous solution including gelatin (manufactured by Nitta Gelatin, Inc.) at a concentration of 0.2 mg/ml and laminin at a concentration of 10 μg/mL was introduced into the cell culture substrate 4 (NC214), and the mixture was left to stand for one hour at 37° C. Subsequently, the aqueous solution was discarded, and the cell culture substrate was dried at room temperature of 25° C. (relative humidity 35% to 55% RH).

Culture of iPS Cells and Evaluation of Detachment Rate

Culture of iPS cells and evaluation of the detachment rate were carried out in the same manner as in example 5.

The results are presented in Table 3.

Furthermore, the culture substrate 4 that had been coated with laminin and dried at room temperature of 25° C. was further left to stand for 1 day or 30 days at room temperature (25° C., 40% RH), and then a similar culturing evaluation test was carried out.

Example 8

This is an example in which the surface of the culture substrate 4 was coated with laminin and subjected to culture without drying.

Production of Culture Substrate

The same cell culture substrate 4 (NC214) as that of Example 6 was used.

Coating of Adhesive Matrix

500 μL (equivalent to a coating amount of 0.5 μg/cm$^2$) of an aqueous solution of laminin (trade name: iMatrix, manufactured by Nippi, Inc.) at a concentration of 10 µg/mL was introduced into the cell culture substrate 4 (NC214), and the mixture was left to stand for one hour at 37° C. The aqueous solution was discarded, and the cell culture substrate was supplied immediately to cell culture without drying.

Culture of iPS Cells and Evaluation of Detachment Rate

Culture of iPS cells and evaluation of the detachment rate were carried out in the same manner as in Example 5.

Comparative Example 1

This is an example in which the surface of a commercially available Petri dish for tissue culture (TCPS) was coated with laminin and subjected to culture without drying, in which a ROCK inhibitor was added to the medium.

Coating of Adhesive Matrix

500 µL (equivalent to a coating amount of 0.5 µg/cm²) of an aqueous solution of laminin (trade name: iMatrix, manufactured by Nippi, Inc.) at a concentration of 10 µg/mL was introduced into a 35-mm Petri dish made of polystyrene (manufactured by AGC Techno Glass Co., Ltd.), and the Petri dish was left to stand for one hour at 37° C. The aqueous solution was discarded, and the Petri dish was supplied immediately to cell culture.

Culture of iPS Cells and Evaluation of Detachment Rate

The detachment rate, survival rate, and culturing performance for iPS cells were evaluated in the same manner as in Example 1, except that a medium containing ROCK inhibitor Y27632 (amount of addition: 0.5 µg/mL of medium) added thereto was used instead of the ReproFF2 medium of Example 1 at the time of cell inoculation.

Comparative Example 2

This is an example in which the surface of a commercially available Petri dish for tissue culture (TCPS) was coated with laminin and subjected to culture without drying, in which a ROCK inhibitor was not added to the medium.

Coating of Adhesive Matrix

500 µL (equivalent to a coating amount of 0.5 µg/cm²) of an aqueous solution of laminin (trade name: iMatrix, manufactured by Nippi, Inc.) at a concentration of 10 µg/mL was introduced into a 35-mm Petri dish made of polystyrene (manufactured by AGC Techno Glass Co., Ltd.), and the Petri dish was left to stand for one hour at 37° C. The aqueous solution was discarded, and the Petri dish was supplied immediately to cell culture.

Culture of iPS Cells and Evaluation of Detachment Rate

The detachment rate, survival rate, and culturing performance for iPS cells were evaluated in the same manner as in Example 1.

Comparative Example 3

This is an example of coating laminin only on the surface of a commercially available Petri dish for tissue culture (TCPS), drying the Petri dish, and then evaluating the Petri dish with StemFit Ak02N medium.

Coating of Adhesive Matrix

500 µL (equivalent to a coating amount of 0.5 µg/cm²) of an aqueous solution of laminin (trade name: iMatrix, manufactured by Nippi, Inc.) at a concentration of 10 µg/mL was introduced into a 35-mm Petri dish made of polystyrene (manufactured by AGC Techno Glass Co., Ltd.), and the Petri dish was left to stand for one hour at 37° C. The aqueous solution was discarded, and the Petri dish was dried at room temperature of 25° C. (relative humidity 35% to 55% RH).

Culture of iPS Cells and Evaluation of Detachment Rate

The detachment rate, survival rate, and culturing performance for iPS cells were evaluated in the same manner as in Example 1, except that StemFit Ak02N medium was used instead of the ReproFF2 medium of Example 1, and StemFit Ak02N medium containing Rock inhibitor Y27632 (amount of addition: 0.5 µg/mL of medium) added thereto was used instead of the medium at the time of cell inoculation.

For the Examples and Comparative Examples, the results are presented in Tables 2 to 4.

TABLE 2

|  | Example 1 | Example 2 | Example 3 | Example 4 |
|---|---|---|---|---|
| Cell culture substrate | MC114 | MC414 | MC814 | MC814 |
| Percentage content of inorganic material (mass %) | 5 | 17 | 29 | 29 |
| Percentage content of PNIPA (mass %) | 17 | 15 | 13 | 13 |
| Laminin (µg/cm2) | 0.05 (dry) | 0.05 (dry) | 0.05 (dry) | 0.05 (dry) |
| Collagen (µg/cm2) | 50 | 50 | 50 | 50 |
| Gelatin (µg/cm2) | — | — | — | — |
| ROCK inhibitor (µmol/cm2) | 0.005 | 0.005 | 0.005 | — |
| Culture container | Culture container 1 | Culture container 2 | Culture container 3 | Culture container 4 |
| Medium | ReproFF2 | ReproFF2 | ReproFF2 | ReproFF2 |
| Culturing performance (in case in which number of cells of Comparative Example 1 is designated as 1.0) | 0.7 | 0.7 | 1.0 | 0.9 |
| AP staining | Positive | Positive | Positive | Positive |
| Cell detachment rate according to enzymatic method (%) | — | — | — | — |
| Cell detachment rate according to temperature control method (%) | 60 | 83 | 85 | 86 |
| Survival rate of cells detached by temperature control (%) | 50 | 80 | 82 | 80 |

TABLE 3

|  | Example 5 | Example 6 | Example 7 | Example 8 |
| --- | --- | --- | --- | --- |
| Cell culture substrate | MC814 | NC214 | NC214 | NC214 |
| Percentage content of inorganic material (mass %) | 29 | 12 | 12 | 12 |
| Percentage content of PNIPA (mass %) | 13 | 88 | 88 | 88 |
| Laminin ($\mu g/cm^2$) | 0.5 (dry) | 0.5 (dry) | 0.5 (dry) | 0.5 (wet) |
| Collagen ($\mu g/cm^2$) | — | — | — | — |
| Gelatin ($\mu g/cm^2$) | — | — | — | — |
| ROCK inhibitor ($\mu mol/cm^2$) | — | — | — | — |
| Culture container | Culture container 5 | Culture container 6 | Culture container 7 | Culture container 8 |
| Medium | StemFit AK02N | StemFit AK02N | StemFit AK02N | StemFit AK02N |
| Culturing performance (in case in which number of cells of Comparative Example 1 is designated as 1.0) | 0.5 | 1.0 | 1.0 | 1.0 |
| AP staining | Positive | Positive | Positive | Positive |
| Cell detachment rate according to enzymatic method (%) | 99 | 91 | 93 | 90 |
| Cell detachment rate according to temperature control method (%) | 90 | 88 | 87 | 85 |
| Survival rate of cells detached by temperature control (%) | 85 | 86 | 85 | 81 |

TABLE 4

|  | Comparative Example 1 | Comparative Example 2 | Comparative Example 3 |
| --- | --- | --- | --- |
| Cell culture substrate | TCPS | TCPS | TCPS |
| Percentage content of inorganic material (mass %) | — | — | — |
| Percentage content of PNIPA (mass %) | — | — | — |
| Laminin ($\mu g/cm^2$) | 0.5 (wet) | 0.5 (wet) | 0.5 (dry) |
| Collagen ($\mu g/cm^2$) | — | — | — |
| Gelatin ($\mu g/cm^2$) | — | — | — |
| ROCK inhibitor ($\mu mol/cm^2$) | — | — | — |
| Culture container | Comparative culture container 1 | Comparative culture container 2 | Comparative culture container 3 |
| Medium | ReproFF2 | ReproFF2 | StemFit AK02N |
| Culturing performance (in case in which number of cells of Comparative Example 1 is designated as 1.0) | 1.0 | 0 (Not culturable) | 1.0 |
| AP staining | Positive | — | Positive |
| Cell detachment rate according to enzymatic method (%) | 10 | — | 50 |
| Cell detachment rate according to temperature control method (%) | 5 | — | 7 |
| Survival rate of cells detached by temperature control (%) | 5 | — | 6 | wet: Laminin was coated, and the cell culture substrate was supplied immediately to cell culture without drying.

dry: Laminin was coated, the cell culture substrate was dried at room temperature (25° C., 40% RH), and then the cell Examples 9 to 12 and Comparative Example 4

Storage Stability Test

Regarding the culture containers 3 and 5 to 7 and Comparative culture container 3 produced as described above, for containers that had been stored for one day at 25° C. and 40% RH and containers that had been stored for 30 days at 25° C. and 40% RH, the detachment rate, survival rate, and culturing performance for iPS cells were evaluated in the same manner as in Example 1, and the results are presented in Table 5.

TABLE 5

|  | Example 9 | Example 10 | Example 11 | Example 12 | Comparative Example 4 |
|---|---|---|---|---|---|
| Culture container | Culture container 3 | Culture container 5 | Culture container 6 | Culture container 7 | Comparative culture container 3 |
| Temperature-controlled cell detachment rate after storage for one day at 25° C. (%) | 85.0 | 90.0 | 88.0 | 85.0 | 7.0 |
| Temperature-controlled cell detachment rate after storage for 30 days at 25° C. (%) | 86.0 | 88.0 | 87.0 | 86.0 | 0 (Not culturable) |

From the Example and Comparative Examples described above, it could be found that culture containers produced using the cell culture substrate of the present invention can achieve a good balance between high culturing performance, detachment properties, and survival rate after detachment.

Furthermore, the culture substrate of the present invention could be suitably used in both a wet state and a dry state, and exhibited high storage stability in a dry state even without the use of extracellular matrices such as collagen and gelatin in combination.

Example 13

Culture of iPS cells and evaluation of the detachment rate were carried out as follows, using the cell culture substrate 4 of Example 6.

That is, 1.5 ml of a medium (StemFit Ak02N, manufactured by Ajinomoto Co., Inc.) to which 4.8 ul of an aqueous solution of laminin (trade name: iMatrix, manufactured by Nippi, Inc.) at a concentration of 0.5 ug/ul, 1.5 ul of ROCK inhibitor Y27632 at a concentration of 3.4 ug/ul, and 1.3× $10^4$ cells of iPS cells (strain 201B7, manufactured by iPS Academia Japan, Inc.) had been added, was introduced into the culture container 4, and the culture container was left to stand in a thermostat at 37° C. in a 5% $CO_2$ atmosphere. Thus, culture was carried out for 8 days. From the third day after the day of initiating culture, the medium was exchanged everyday for consecutive 5 days.

Next, medium exchange was carried out with a cold medium at 4° C., the culture container was left to stand for 10 minutes at room temperature, and then a "pipetting operation" of sucking in and out the medium with a pipette was performed about 10 times. Thus, cell detachment was carried out. The cell culturing performance determined according to the above-described methods of "Detachment rate and survival rate of cells, and measurement of culturing performance" was 1.0 (equivalent to TCPS), the cell detachment rate was 85%, and the survival rate of the harvested cells was 70%.

Comparative Example 5

Culture of iPS cells and evaluation of the detachment rate were carried out in the same manner as in Example 13, except that a 35-mm Petri dish made of polystyrene (35 mm/Tissue Culture Dish, manufactured by Iwaki Cell Biology Corp.) was used. As a result, the cell culturing performance was 1.0, the cell detachment rate was 5%, and the survival rate of harvested cells was 20%.

INDUSTRIAL APPLICABILITY

With the cell culture substrate of the present invention, even human pluripotent stem cells can be cultured with high efficiency, and the cells after culturing can be detached and harvested while maintaining a high survival rate. Therefore, the cell culture substrate can be suitably used for use applications, for example, a cell culture substrate directed to regenerative medicine.

The invention claimed is:

1. A stem cell culture substrate comprising: a polymer having a lower critical solution temperature; one or more inorganic materials selected from a water-swellable clay mineral and silica; and an adhesive matrix, wherein the adhesive matrix is an extracellular matrix and/or an adhesive synthetic matrix,
   wherein the extracellular matrix is at least one selected from laminin, fibronectin, vitronectin, cadherin, and fragments thereof, and
   wherein the stem cell culture substrate has an average film thickness of 1,000 nm or less.

2. The stem cell culture substrate according to claim 1, wherein the adhesive synthetic matrix is poly[2-(methacryloyloxy)ethyl dimethyl-(3-sulfopropyl) ammonium hydroxide] or an oligopeptide-supporting polymer.

3. The stem culture substrate according to claim 1, wherein the polymer having a lower critical solution temperature is a polymer obtainable by polymerizing a monomer that gives a homopolymer having a lower critical solution temperature, and the monomer that gives a homopolymer having a lower critical solution temperature is at least one selected from N-isopropyl (meth)acrylamide, N-n-propyl (meth)acrylamide, N-cyclopropyl (meth)acrylamide, N-ethoxyethyl (meth)acrylamide, N-tetrahydrofurfuryl (meth)acrylamide, N-ethylacrylamide, N-ethyl-N-methylacrylamide, N,N-diethylacrylamide, N-methyl-N-n-propylacrylamide, N-methyl-N-isopropylacrylamide, N-acryloylpiperidine, and N-acryloylpyrrolidine.

4. The stem cell culture substrate according to claim 1, wherein
   the polymer having a lower critical solution temperature is at least one of
   a copolymer (B1) of a monomer (a) represented by the following Formula (1) and a hydrophilic amide-based vinyl monomer (b),
   a copolymer (B2) of the monomer (a) and a monomer (c) represented by the following Formula (2), or a copolymer (B3) of monomer (a) and a polyethylene glycol chain-containing monomer (d) represented by the following Formula (3), and
   the percentage content of the polymer having a lower critical solution temperature with respect to the total amount of the cell culture substrate is 5% by mass to 99% by mass:

[Chem. 1]

$$CH_2=CR_1 \\ | \\ COOR_2OR_3 \quad (1)$$

wherein $R_1$ represents a hydrogen atom or a methyl group; $R_2$ represents an alkylene group having 2 or 3 carbon atoms; and $R_3$ represents an alkyl group having 1 or 2 carbon atoms,

[Chem. 2]

$$CH_2=CR_4 \\ | \\ COOR_5OH \quad (2)$$

wherein $R_4$ represents a hydrogen atom or a methyl group; and $R_5$ represents an alkylene group having 2 or 3 carbon atoms, and

[Chem. 3]

$$CH_2=CH \\ | \\ CO(OCH_2CH_2)_nOCH_3 \quad (3)$$

wherein n represents an integer of 2 to 20.

5. The stem culture substrate according to claim 4, wherein the hydrophilic amide-based vinyl monomer (b) is at least one monomer selected from the group consisting of an N-substituted (meth)acrylamide derivative, an N,N-disubstituted (meth)acrylamide derivative, and N-vinylpyrrolidone.

6. The stem cell culture substrate according to claim 1, further comprising a polymer (A) of the monomer (a) represented by the following Formula (1)

$$CH_2=CR_1 \\ | \\ COOR_2OR_3 \quad (1)$$

wherein $R_1$ represents a hydrogen atom or a methyl group; $R_2$ represents an alkylene group having 2 or 3 carbon atoms; and $R_3$ represents an alkyl group having 1 or 2 carbon atoms.

7. The stem culture substrate according to claim 1, wherein the water-swellable clay mineral is one or more clay minerals that delaminate into 1 to 10 layers in an aqueous medium (W), the water-swellable clay mineral being selected from water-swellable hectorite, water-swellable montmorillonite, water-swellable saponite, and water-swellable synthetic mica, and the silica is water-dispersible colloidal silica.

8. The stem cell culture substrate according to claim 1, wherein the cell culture substrate comprising a polymer having a lower critical solution temperature further includes thereon at least one protein selected from gelatin, collagen, and/or albumin.

9. The stem cell culture substrate according to claim 8, wherein a polymer having a lower critical solution temperature; at least one protein selected from gelatin, collagen, and/or albumin; and an adhesive matrix are laminated in sequence.

10. The stem cell culture substrate according to claim 1, wherein the cell culture substrate is a dry cell culture substrate.

11. The stem cell culture substrate according to claim 1, wherein the cell culture substrate is laminated on a supporting medium.

12. A method for producing a dry stem cell culture substrate, the method comprising:
a step of coating a solution including at least one protein selected from gelatin, collagen, and/or albumin on a polymer having a lower critical solution temperature;
a step of further coating a solution including the adhesive matrix according to claim 1 to obtain a cell culture substrate; and
a step of drying the obtained stem cell culture substrate.

13. A cell culture equipment, comprising a supporting medium and the stem cell culture substrate according to claim 1.

* * * * *